(12) United States Patent
Agrawal et al.

(10) Patent No.: US 9,750,420 B1
(45) Date of Patent: Sep. 5, 2017

(54) FACIAL FEATURE SELECTION FOR HEART RATE DETECTION

(71) Applicant: Amazon Technologies, Inc., Reno, NV (US)

(72) Inventors: Amit Kumar Agrawal, Santa Clara, CA (US); Wei Li, Cupertino, CA (US); Nicholas Jialei Su, Stanford, CA (US); Ambrish Tyagi, Palo Alto, CA (US)

(73) Assignee: AMAZON TECHNOLOGIES, INC., Seattle, WA (US)

( * ) Notice: Subject to any disclaimer, the term of this patent is extended or adjusted under 35 U.S.C. 154(b) by 505 days.

(21) Appl. No.: 14/566,152

(22) Filed: Dec. 10, 2014

(51) Int. Cl.
*A61B 5/00* (2006.01)
*A61B 5/024* (2006.01)
*G06K 9/00* (2006.01)

(52) U.S. Cl.
CPC ........ *A61B 5/02427* (2013.01); *G06K 9/0061* (2013.01); *G06K 9/00234* (2013.01); *G06K 9/00281* (2013.01)

(58) Field of Classification Search
CPC combination set(s) only.
See application file for complete search history.

*Primary Examiner* — Joseph M Santos Rodriguez
(74) *Attorney, Agent, or Firm* — Pierce Atwood LLP

(57) ABSTRACT

The location of a user's head, for purposes such as head tracking or motion input, can be determined. For example, a computing device (e.g., a tablet, mobile phone, etc.) can utilize one or more detectors or other image classifiers to detect the presence objects such as features of the face in images captured by one or more cameras of the computing device. Based on the detected feature(s), the subject technology provides embodiments for detecting a heart rate of the user of the computing device without requiring invasive procedures or addition sensors on the computing device by selecting a region of interest for analyzing color or other image data measurements over a period of time. Changes in color at the select region of interest may be further processed to extract a user's heart rate using techniques described further herein.

20 Claims, 10 Drawing Sheets

FACIAL FEATURE SELECTION FOR HEART RATE DETECTION

BACKGROUND

As the functionality offered by computing devices continues to improve, users are utilizing these devices in different ways for an increasing variety of purposes. For example, certain devices utilize one or more cameras to attempt to detect motions or locations of various objects, such as for head tracking or motion input. In various head tracking approaches, the device needs to first detect whether an image (i.e., portion thereof) contains the user's face. However, facial detection is not a trivial task and many conventional facial detection techniques are imperfect due to the wide range of objects that may be contained in an image and due to the limited time frame that is usually available for detecting the presence of a face. Further, conventional object recognition approaches are resource and power intensive, which can be problematic for portable devices where power and battery life is limited. Further still, biometric readings are becoming more prevalent and such functionality may be provided by a given computing device.

BRIEF DESCRIPTION OF THE DRAWINGS

Various embodiments in accordance with the present disclosure will be described with reference to the drawings, in which.

DETAILED DESCRIPTION

Figure 1:
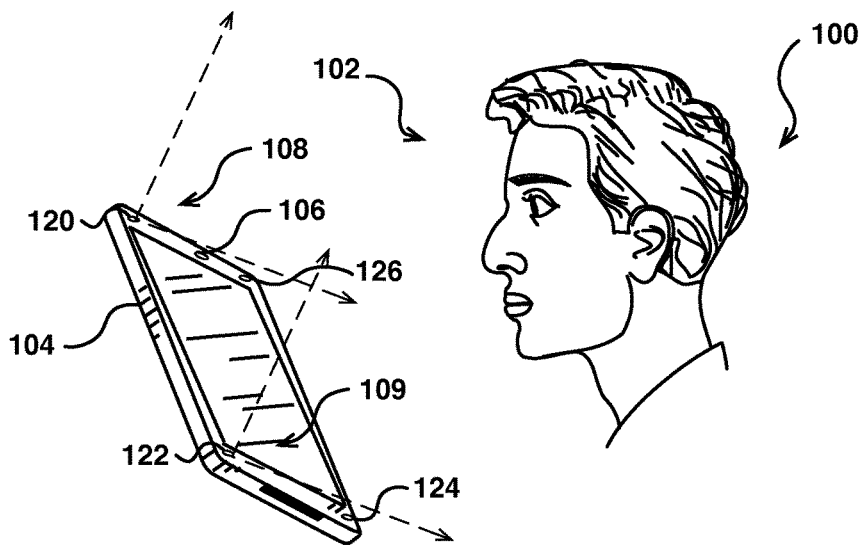
FIG. 1 illustrates an example of a user interacting with a device in accordance with various embodiments.

Systems and methods in accordance with various embodiments of the present disclosure may overcome one or more of the aforementioned and other deficiencies experienced in conventional approaches to determining objects and features, such as features of a user's face. In particular various embodiments, a computing device (e.g., a tablet, mobile phone, etc.) can utilize one or more detectors or other image classifiers to detect the presence objects such as features of the face in images captured by one or more cameras of the computing device. Such a computing device may provide one or more cameras for detecting features of the user's face such as eyes, nose, mouth, etc. Based on the detected feature(s), the subject technology provides embodiments for detecting a heart rate of the user of the computing device without requiring invasive procedures or addition sensors on the computing device by selecting a region of interest for analyzing color or other image data measurements over a period of time. Changes in color at the select region of interest may be further processed to extract a user's heart rate using techniques described further herein.

In an embodiment, more than one region of the user's face may be analyzed to extract different measurements for performing heart rate detection. In an example, a region covering an area near an eye of the user (e.g., 2 inches above the right eye) may be measured over time, and another region near the cheek of the user (e.g., 2 inches below the right eye) may be measured over time to determine changes in color. Such color measurements may be further combined (e.g., averaged) in order to provide potentially more accurate values for heart rate detection (e.g., to eliminate outliers, etc.). Further, these regions may be tracked concurrently using multiple cameras of the computing device. Thus, the subject technology may leverage the presence of multiple cameras in a given computing device to potentially improve heart rate detection.

In certain embodiments, a pair of cameras having at least partially overlapping fields of view can detect the presence of an object, such as a face of a user, facial features of the user, and/or other features represented in image data captured by the cameras. It should be noted that although approaches are described with respect to a pair of cameras, in accordance with various embodiments such approaches can apply to a one camera capturing one or more images or to a plurality of cameras each capturing one or more images. In this example, portions of at least a first image acquired by a first camera of the stereo camera pair and a second image acquired by a second camera of the stereo camera pair can be analyzed to attempt to identify feature points corresponding to facial features of the user's face or other objects represented in the images. For example, the image data capture by a first camera of the pair of cameras can be analyzed by a first set of detectors to detect a right eye of a user of the computing device, where each detector of the first set of detectors can detect the right eye using a different approach. The image data captured by a second camera of the pair of cameras can be analyzed by a second set of detectors to detect the left eye of the user, where like the first set of detectors, each detector of the second set of detectors can detect the left eye using a different approach. The different approaches can include using different sized windows to detect facial features, different starting positions of the windows, etc. Other approaches can be used as well, such as to use shape, template, or object recognition processes. In some embodiments, an object location algorithm might look for objects in the image data that meet a certain object detection criterion, such as objects (e.g., areas of a relatively common intensity in an image) of a certain size, shape, and/or location. In some embodiments, the image data represents infrared (IR) light emitted by the device, reflected by the object, and detected by the device.

For at least a portion of the detectors used to detect the right eye and a portion of the detectors used to detect the left eye. Various other functions and advantages are described and suggested below as may be provided in accordance with the various embodiments.

FIG. 1 illustrates an example situation 100 wherein a user 102 is viewing and/or interacting with a computing device 104. Although a portable computing device (e.g., a smart phone, an e-book reader, or tablet computer) is shown, it should be understood that various other types of electronic device that are capable of determining and processing input can be used in accordance with various embodiments discussed herein. These devices can include, for example, notebook computers, personal data assistants, cellular phones, video gaming consoles or controllers, smart televisions, a wearable computer (e.g., a smart watch or glasses), and portable media players, among others. In this example, the computing device 104 has a front-facing capture element 106, such as a camera operable to perform functions such as image and/or video capture. In accordance with the illustrated embodiment, the device further includes a rear-facing camera and four corner cameras (120, 122, 124, and 126) also located on the front of the device. These cameras can be used to acquire images and the image information for each image can be used by the device to determine a relative position and/or orientation of the user with respect to the device. Such image information can also be used for object recognition, object tracking, or various other purposes such as various calibration processes that can be used to adjust for any misalignment between the cameras.

It should be understood, however, that there can be additional and/or alternative cameras placed in similar or alternative locations in accordance with various embodiments, and that information from any or all of these cameras can be analyzed as appropriate. For example, a computing device might have a high resolution still camera that is able to capture images useful for performing facial recognition, and might have a lower resolution video camera that can be useful for performing object detection. In other embodiments, a single camera might be used to capture image information for both types of analysis, while still other embodiments might utilize stereo cameras or other elements to determine distance information or perform three dimensional modeling, among other such aspects. As mentioned, some devices might have digital still cameras that are able to capture single images at specific points in time, or digital video cameras that are able to continuously capture image information, which can be referred to as a set of frames in at least some embodiments. Also, for a process such as image recognition to be relatively accurate, the image being analyzed may have to meet some minimum criteria. This can include, for example, adequate lighting and contrast, but can also include factors such as quality of focus and spatial resolution. Accordingly, a device can include additional elements as well, such as illumination elements and focusing optics as discussed elsewhere herein. Each camera may be, for example, an imaging element including a complimentary metal-oxide semiconductor (CMOS) device, a motion detection sensor, a charge coupled device (CCD), an infrared sensor, a quantum dot imager, a gallium arsenide sensor, or any other appropriate image capturing technology.

As mentioned, the device can include stereo cameras on the front or back of the device to perform stereoscopic or three-dimensional (3D) imaging. These cameras are separated by a distance sufficient to enable stereoscopic imaging over at least a determined distance, each with a determined field of view that at least partially overlaps. In some embodiments the stereo cameras each come with auto-focusing mechanisms, enabling the cameras to focus to different depths. When capturing a stereoscopic ("stereo") image, each of the pair of cameras captures an image at approximately the same time. The offset of the cameras will cause the location of objects in each image to be slightly offset, where the amount of offset is a factor of the separation of the cameras and the distance from the cameras to the objects. This varying offset with distance, otherwise known as disparity, provides the perception of depth in the image when the images are combined using a stereovision process.

Figure 2A:
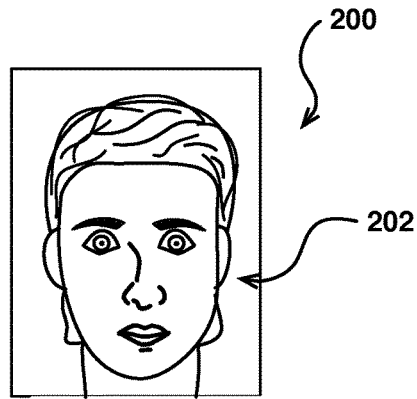
FIGS. 2A, 2B and 2C illustrate an example of how a device might use an image to perform head tracking in accordance with various embodiments.

In this example, the device 104 is analyzing image data captured by one or more cameras of the device. For example, as illustrated in example 200 of FIG. 2A, a user 202 is represented in image data captured by, for example, a front-facing camera 106. In accordance with various embodiments, the image data can be analyzed to estimate the head center of the user or location of another feature of the user. Conventional approaches utilize model based approaches. An example model based approach is active shape model (ASM). In this approach, a model of several facial feature locations and their relationship with image intensities around the feature points is learned. The model is learned, for example, using training images. During runtime, given an image, the model is applied to obtain the best fit of 'all' the facial features to the given image. Another approach includes constrained local models (CLM). In this approach, detectors are applied to detect different features on the face independently. For example, in such approaches a different detector is trained for the right eye, left eye, mouth, etc. Typically, there is a single detector for each landmark and the detectors are applied to the image and a model is fitted to the detector responses to obtain the best fit of all facial features to the given face image. However, these approaches can be resource intensive and may not work in various situations. Accordingly, in accordance with various embodiments, facial feature can be detected using multiple tuned detectors. The facial feature can be, for example, the location of eyes, location of mouth, nose or any identifiable feature on the human face. Several detectors can be trained for a chosen feature. At run time, at least a portion of the detectors can be applied. In various embodiments, the detectors can be associated with a confidence value. The detectors can provide an estimate of the head center of the user and the estimates can be combined according to their confidence value or otherwise combined to obtain the final head center location.

Figure 2B:
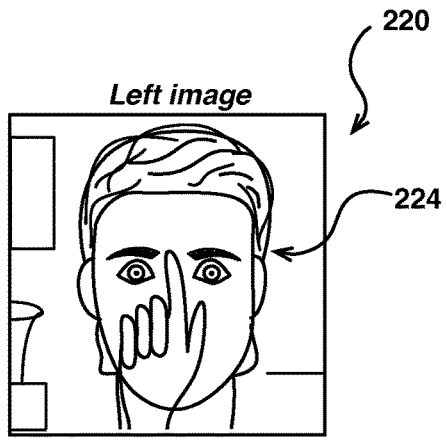
Figure 2C:
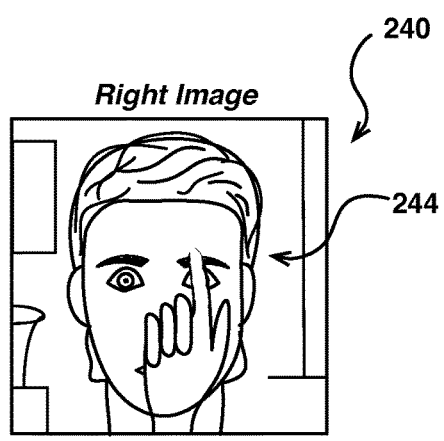

In various other embodiments, image data captured by two or more image capture elements, for example, image capture elements 120 and 122, can be used to determine the relative position of the user's head to the device, in order to determine how to render content on a display of the device or perform another such action. For example, as illustrated in the example 220 of FIG. 2B, a user 224 is represented in an image captured by camera 120 of the device, here displayed for simplicity of explanation, although such display is not utilized in many embodiments. As illustrated, the head and shoulders of the user are represented in the image. As illustrated in example 240 of FIG. 2C, the user 244 is represented in an image captured by camera 122 of the device.

In some situations a portion of the user may not be captured in the image data. It is also possible that a portion of the head may be obscured, such as by being at least partially occluded by a portion of the camera aperture, or may be located in shadow or otherwise unavailable or unsuitable for imaging and/or analysis. In order to determine the position of the user, it is necessary to first identify corresponding features, such as facial features of the user. For example, in conventional approaches, a pair of cameras that are configured to capture stereoscopic image data such that the disparity information can be used to determine, in three dimensions, the relative location of the head to the device. The pair of cameras can be part of a single camera assembly that can be used to capture stereoscopic images, or other types of three-dimensional data, where offsets in position (or disparity) due to the offset of the cameras can be used to calculate distance, and can be used to render an image that appears to a user to show objects at their respective distances.

Accordingly, an approach can be utilized that can locate approximate head position in cases where the head is partially occluded as well as cases where the head is not occluded. For example, in accordance with various embodiments, a computing device (e.g., a tablet computer, mobile phone, etc.) can utilize one or more detectors or other image classifiers to detect the presence of a face or features of the face in images captured by a pair of cameras of the computing device.

Figure 3A:
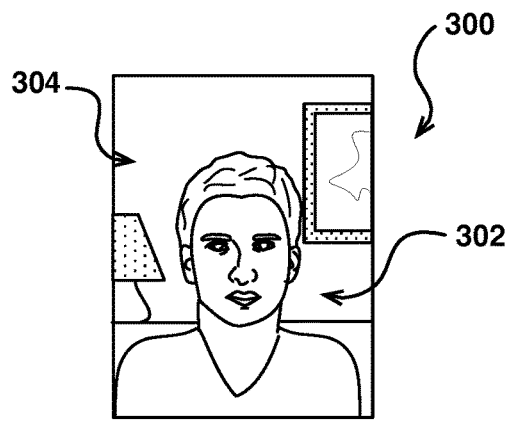
FIGS. 3A, 3B, 3C, 3D, and 3E illustrate an example approach to determining a portion of an image corresponding to a user's head that can be utilized in accordance with various embodiments.
Figure 3B:
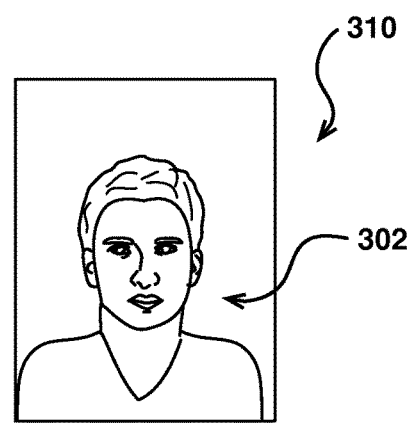

FIGS. 3A through 3E illustrate an example approach for locating the head of a user or viewer in at least some embodiments. FIG. 3A illustrates an example image 300 that can be captured by a camera of a computing device in accordance with various embodiments. As discussed, this can include a three-dimensional or stereoscopic image, or image data, captured by at least one pair of cameras or a stereo camera assembly on the computing device. It should be noted that although an image captured from a single camera is described, embodiments described herein are not limited to such as arrangement, and those skilled in the art will appreciate that more cameras can be used. It should be further noted, that although features of a user's face are detected and used in such approaches, any object or features a known or approximated distance from the device can be used in the various approaches described herein. These objects can include a hat the user is wearing, sunglasses, clothing, text on the clothing, jewelry, among other objects that can be detected on and/or proximate to the user.

As illustrated, there is a representation of a user 302 and representations of several other objects 304 in the image. As described, when using a computing device, a user will typically be within a determined distance of the device, such as within about three feet of the device. The distance of the user or the presence of the user can be determined using a camera assembly that includes an infrared (IR) emitter and capture reflected IR such that distance can be inferred by the relative intensity of the reflected IR. In other embodiments, a camera assembly might include a proximity sensor or distance sensor, for example, such that the camera assembly can provide both image and distance data, which can be used to calculate three-dimensional position information. A proximity or distance sensor can include, for example, an ultrasonic sensor, an electromagnetic sensor, a capacitive sensor, a magnetic sensor, and the like, which is able to determine a distance to one or more objects with respect to the sensor. Various other types of camera assemblies can be used as well within the scope of the various embodiments.

In some embodiments, the user can also be determined to typically be at least a determined distance from the device, such as at least 30 cm, or at least six inches. In this example, if more than one such object exists, the largest object can be selected as the user, although other approaches can be used as well, such as to use shape or object recognition processes. For example, an object location algorithm might look for objects in the image data that meet a certain object detection criterion, such as objects (e.g., areas of a relatively common intensity in an image) of a certain size, shape, and/or location. Object templates such as head tracking templates can be used to determine an outline of a head of the user of the computing device. For example, a "head and shoulders" signature or pattern can be compared against the contour to attempt to determine whether the contour resembles a representation of a user. As an example, there might be a range of relative head, neck, and shoulder positions, shapes, ratios, and/or sizes, and the contour must match and/or fit within these ranges.

In various embodiments, when attempting to detect a face within an image, at first, the size of the face is unknown. As such, a range of different scales can be hypothesized and the device can attempt to find the face at one or more of the different scales. For example, if a face of a particular size or scale is hypothesized, the framework can take sub-portions of the image (e.g., smaller window within the image) that correspond to the hypothesized scale. For example, if the size of the hypothesized face corresponds to a 50×50 pixel sub-portion of the image, the device can begin by first analyzing the first upper-left corner 50×50 pixel sub-portion of the image and to test the sub-portion for the presence of a face. If a face is not detected, the sub-image can be shifted by one pixel along the column (keeping rows the same) and analyze that shifted sub-image. It will be apparent to one of ordinary skill in the art that the starting position and direction in which the sub-portion is shifted can easily be changed. For example, in alternative embodiments, the framework may first begin the bottom right corner of the screen, or may shift the sub-image along the rows while keeping the columns the same and so on.

In accordance with an embodiment, once the portions of the images containing faces have been extracted, the portion of the image containing the face can be normalized. In accordance with an embodiment, normalizing can involve adjusting the size (i.e., rescaling) of the images to a common size, for example, a 36×36 pixel image. Various approaches can be used to rescale an image as may include bilinear and bicubic interpolation algorithms. It should be noted that various other algorithms can be as is known in the art. The outline or presence of the user's head can be used to identify a foreground portion, and a background or remaining portion of the image can be removed, such as is illustrated in the image state 310 of FIG. 3B. It should be understood that the image in FIG. 3B, as well as other images shown, do not need to be created and are presented for purposes of explanation, as in many cases the image data will be analyzed and processed without generating proper images for display.

Figure 3C:
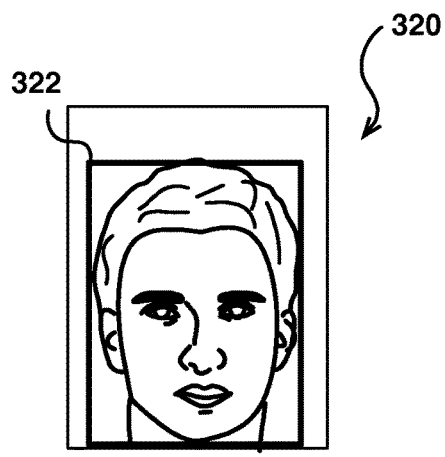

As illustrated in FIG. 3C, at least some embodiments can utilize a face or head detection algorithm as discussed above to attempt to locate an approximate head or face position in a captured image or video frame 320. In accordance with various embodiments, approaches to detect a head or face of a user include, for example, the Viola-Jones object detection framework. The Viola-Jones framework is a technique proposed in 2001 by Paul Viola and Michael Jones to detect objects such as faces. This technique is efficient as it provides object detection rates in real-time or near real-time. Viola-Jones detection uses image gradient cues by implementing Haar wavelet computation. Haar wavelets are features that are employed by the Viola-Jones framework to detect objects. Haar wavelets are determined by computing sums of image pixels within rectangular areas. The object detection framework also employs a variant of the learning algorithm AdaBoost to both select the best features (e.g., Haar wavelets) and to train classifiers that use them. In some embodiments, a computing device might utilize one or more motion sensors, such as an electronic gyroscope or inertial sensor, to attempt to assist with location determinations. For example, a rotation of a device can cause a rapid shift in objects represented in an image, such that image stabilization might not be attempted if the amount of motion exceeds a determined amount. For smaller movements, the information from the motion sensors can be used to provide a starting point for the feature detection in a subsequent image, which can increase the speed of the detection process and reduce the amount of processing and power required. Various other types of movement or motion information can be used as well within the scope of the various embodiments.

Figure 3D:
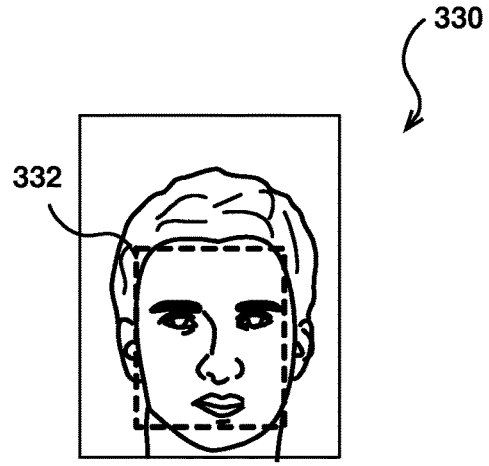
Figure 3E:
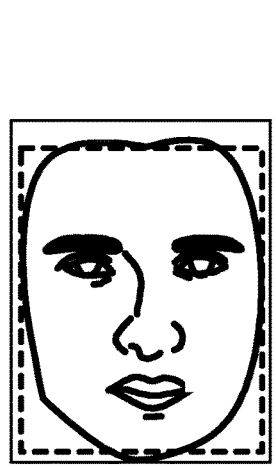

Once the facial region to be analyzed is determined, one or more head or face detection algorithms can be used to identify a region of the user's face. For example, FIG. 3D illustrates an example situation 330 where a head or face detection algorithm has been used to attempt to locate a portion of the image 332 that corresponds to the approximate facial features of the user's face. The head or face detection algorithm can include any appropriate algorithm known or used for such purposes, such as a template matching algorithm, a neural network algorithm, a Fisher linear discriminant algorithm, a maximal rejection classifier algorithm, a support vector machine algorithm, an edge filtering algorithm, an edge detection algorithm, and the like. The ability to locate the head position in an image can reduce the amount of resources otherwise needed to perform facial recognition, as the analysis can be performed only on the portion of the image corresponding to the head position. Further, in some embodiments facial recognition might not be performed unless a head or face can first be detected in the captured image. In this example, the detected head portion, as shown in example 340 of FIG. 3E, can be analyzed using one or more detectors or other facial recognition algorithms to attempt to identify facial features of the person represented in the image to be utilized in various embodiments described herein.

In accordance with various embodiments, the detectors can determine the facial features using a number of different approaches. This can include, for example, identifying unique or distinguishing points such as feature points, facial marks, geometric shapes or distances, or other such features on the face. Example facial recognition algorithms can include, for example, a linear discriminate analysis algorithm, a Fisherface algorithm, a Hidden Markov model-based algorithm, a principal component analysis algorithm, and a neuronal motivated dynamic link matching algorithm, among others. In certain embodiments, specially trained Haar classifiers or other like classifiers can be used to detect the facial features. It should be noted that any number of algorithms can be used, as known to those skilled in the art. In various embodiments, the facial features can include at least one of an eye, mouth, nose, among other facial features.

Figures 4A, 4B:
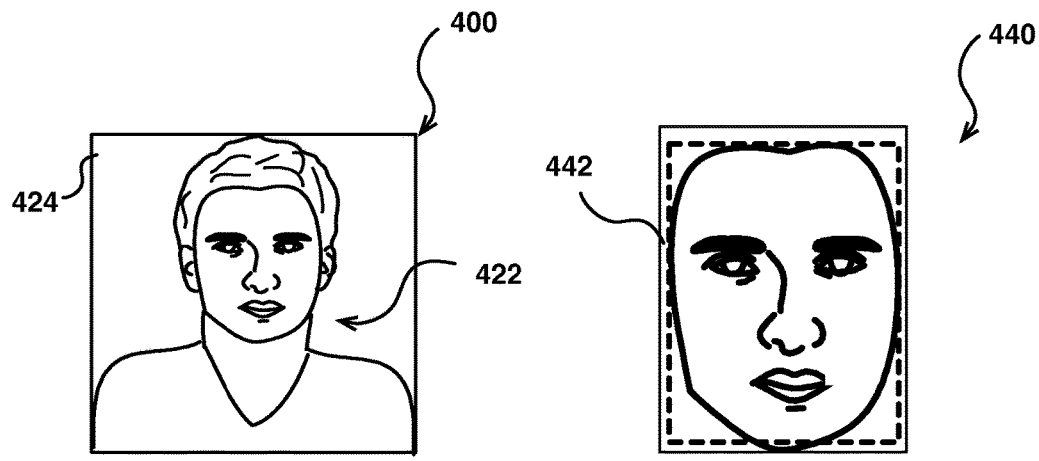
FIGS. 4A, 4B, 4C, and 4D illustrate example approaches to determining a bodily feature of a user that can be used for head tracking in accordance with various embodiments.

As described, in accordance with various embodiments, image data from multiple cameras, such as a stereoscopic camera pair can be used to determine a location of a user's head. As described, these cameras are separated by a distance sufficient to enable stereoscopic imaging over at least a determined distance, each with a determined field of view that at least partially overlaps. The offset of the cameras will cause the location of objects in each image to be slightly offset, where the amount of offset is a factor of the separation of the cameras and the distance from the cameras to the objects. This varying offset with distance, otherwise known as disparity, provides the perception of depth in the image when the images are combined using a stereovision process. In some situations, however, given the different form factors of many computing devices, the separation of the cameras on the device may not allow for the a same feature in image data captured by a first camera to be detected in image data captured by a second camera. For example, as illustrated in example 400 of FIG. 4A, a portion of the user 422 is represented in an image captured by a camera of the device, here displayed on a display screen 424 of a computing device for simplicity of explanation, although such display is not utilized in many embodiments. As illustrated, a portion of the head and shoulders of the user are represented in the image. In some approaches, in order to determine the position of the user, it may be necessary to first identify corresponding features, such as facial features of the user.

In accordance with various embodiments, a computing device (e.g., a tablet computer, mobile phone, etc.) can utilize one or more detectors or other image classifiers to detect the presence of a face or features of the face in images captured by a pair of cameras of the computing device. For example, as illustrated in example 440 of FIG. 4B, the device can utilize a face or head detection algorithm as discussed above to attempt to locate an approximate head or face region 442 of a user in a captured image or video frame. Once the face region is determined, the detectors can be used to detect features of the user For example, the face region 442 can be analyzed by a first set of detectors as shown in example 460 of FIG. 4C. It should be noted that for simplicity, embodiments are described with respect to one camera and image data captured by the camera. However, in accordance with various embodiments, image data captured from other cameras can concurrently be processed and utilized in embodiments described herein. For example, a second camera can concurrently capture image data and the image data can be processed in a similar manner. In the context of capturing image data in a concurrent manner, the image data may be captured within a specified period of time (e.g., milliseconds, etc.) or clock cycles between one camera and another camera. In accordance with various embodiments, a detector can be a machine trained classifier that can be trained to detect particular features in image data of a user such as a right eye, a left eye, nose, mouth, among other features.

Such a supervised learning approach can analyze features of the various images to attempt to identify features that can accurately predict or identify corresponding features of faces in other images. The classifiers can be trained from positive examples of persons and features of those persons represented in images and negative examples of images with no persons. In various embodiments, the classifiers can be trained from image data that includes one or more bodily or other features or from negative example image data that includes other feature types. Application of the classifiers to an input image can be used to detect particular features. In some embodiments, using a detector can include analyzing an image using template matching to determine predetermined features. In this example, template matching is based on matching a pre-defined face pattern or parameterized function to locate a particular feature within an image. Templates are typically prepared manually "offline." In template matching, correlation values for the head and facial features are obtained by comparing one or more templates to an input image, and the presence of a face is determined from the correlation values. In the context of heart rate detection, the classifiers may also be trained to recognize patches of uniform skin or texture that may be likely candidates for regions of interest to measure for heart rate detection (as further described herein).

The detectors can be different shapes and sizes. The shapes can include, for example rectangles, squares, circles, polygons, etc. The sizes can be measure in pixels or some other unit, where the sizes include a width, height, radius, and/or some other indicator of size. Further, each detector can be associated with a different or initial position when analyzing the image to detect a facial feature. For example, a first detector can begin at a first set of image coordinates and a second detector can being at a second set of image coordinates. In various embodiments, more than one detector can be trained to detect the same feature. For example, detector 462 and 468 can be used to detect a right eye while detector 464 can be configured to detect a left eye and detector 466 can be configured to detect a nose. In another example, the detector 462 can be used to detect a forehead while the detector 468 can be used to detect the right eye, the detector 464 can be used to detect a left or right cheek, and the detector 466 can be used to detect the nose. It is contemplated that the detectors may be configured to detect certain features of the face and still be within the scope of the subject technology.

Figures 4C, 4D:
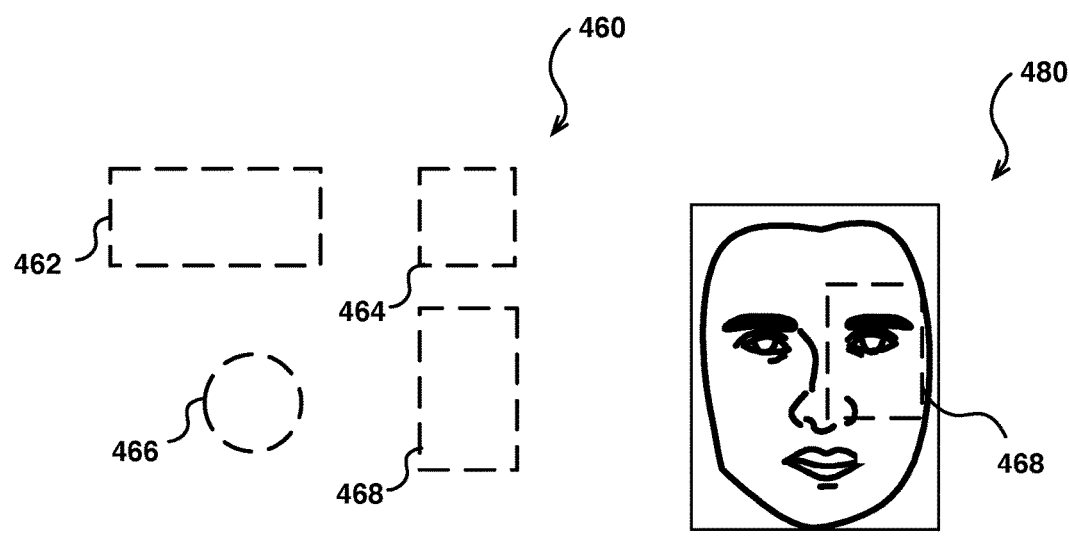

Example 480 of FIG. 4D illustrates the situation where detector 468 is used to detect a right eye of a user. In this example, the detector may traverse the image from an initial starting position until a right eye is detected. Moreover, the process can continue for a number of different detectors. For example, different detectors can be used to detect the right eye of a user in an image. Using an image captured by a camera a first detector can detect the right eye of the user, a second detector can detect the right eye of the user, and a third detector can detect the right eye of the user. As described before, the detectors can be different sizes, shapes, and be associated with a different initial position. It should be further noted that other features can be detected as well as described above. In this regard, detectors can be used to detect a nose, mouth, forehead, cheek, chin, jaw or other feature of the user. It should be also noted that multiple images can be captured and the process can be repeated on at least a portion of the images. In various embodiments, a pair of stereoscopic images can be used. In this situation, a first image captured by a first camera is used and a second image captured by a second camera may be used.

The detectors can use a number of approaches to detect a feature. This can include identifying unique or distinguishing points, facial marks, geometric shapes or distances, or other such features on the face. Example facial and/or feature recognition algorithms can include, for example, a linear discriminate analysis algorithm, a Fisherface algorithm, a Hidden Markov model-based algorithm, a principal component analysis algorithm, and a neuronal motivated dynamic link matching algorithm, among others. Other object recognition processes can be used as well within the scope of the various embodiments. These can include, for example, appearance-based processes that search for features such as edges, changes in lighting or color, or changes in shape or size. Various other approaches utilize gradient generation and matching or histogram analysis for object recognition. Other approaches include feature-based approaches, such as may utilize interpretation trees, geometric hashing, or invariance analysis. Algorithms such as scale-invariant feature transform (SIFT) or speeded up robust features (SURF) algorithms can also be used within the scope of the various embodiments. For computer vision applications, a bag of words or similar approach can also be utilized.

In accordance with various embodiments, the detectors can be hardware accelerated using an ASIC, SoC, FPGA, GPU, or custom designed chip which can allow for significant speed up in detection. In various embodiments, temporal information can be used to specify a region of interest using previous frames or in choosing which detectors to run at given frame based on previous frames. For example, the device can detect a first feature at a first location in a first image and attempt to detect the first feature at the same or approximate location in a second image.

In some embodiments, a pair of cameras having at least partially overlapping fields of view can be used as well. In this example, portions of at least a first image acquired by a first camera of the stereo camera pair and a second image acquired by a second camera of the stereo camera pair can be analyzed to attempt to identity feature points corresponding to facial features of the user's face or other objects represented in the images. For example, the image data captured by a first camera of the pair of cameras can be analyzed by a first set of detectors to detect a right eye of a user of the computing device, where each detector of the first set of detectors can detect the right eye using a different approach. The image data captured by a second camera of the pair of cameras can be analyzed by a second set of detectors to detect the left eye of the user, where like the first set of detectors, each detector of the second set of detectors can detect the left eye using a different approach.

In at least one embodiment, a selection of a region of interest for heart rate detection may be performed based on a location of a detected feature in conjunction with a distance or offset from the location of the detected features. A location of the detected feature may be represented as a set of Cartesian coordinates (e.g., x and y coordinates for two dimensions), and a distance or offset from the location may be determined using a number of pixels that are positive or negative from the Cartesian coordinates. For example, an offset from a location of (0,0) coordinates may be +10 pixels in the X axis and +10 pixels in the Y axis so that the coordinates of the location at the offset is (10,10). In addition, the region of interest may have a center point that is determined based on the offset from the location of the detected feature. For heart rate detection, depending on various factors, such as a time of day, lighting, angle of view, occlusion on the user's face, etc., a region of interest may be selected from a different portion of the user's face from the detected feature(s) that may improve the detection of the user's heart rate. The offset may be determined using an average distance (e.g., from a set of distances from a facial feature) and optionally including a standard deviation of such distances from the detected feature. In an example where the user's left or right eye is detected, an offset distance to a center of a person's forehead may be determined using the average distance and may be further adjusted using the standard deviation. Alternatively or additionally, a region of interest may be selected using knowledge of human anatomy such as locations of facial foramen and/or corresponding locations of arteries or veins on the human face. As an example, a region of interest may be selected at known locations of facial foramen or arteries or veins found in or around the forehead, cheek, chin, jaw, etc., that are located a distance away from the detected feature (e.g., left or right eye, nose, mouth, etc.). Facial foramen (or in its plural word form, foramina) refers to any opening(s). Foramina inside the human body typically allow muscles, nerves, arteries, veins, or other structures to connect one part of the body with another. The skulls of vertebrates, including the human skull, have numerous foramina in which nerves, arteries, veins and other structures pass.

Figure 5A:
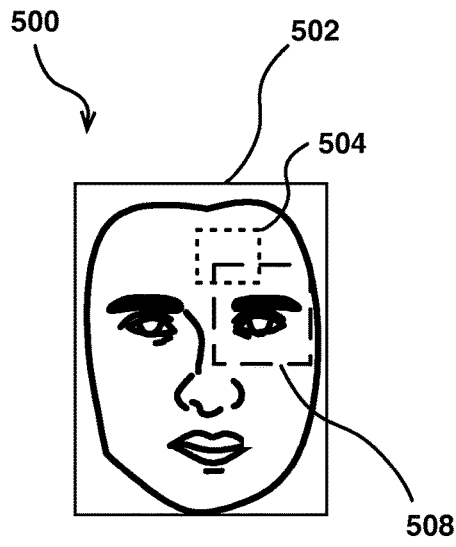
FIG. 5A illustrates an example for detecting a representation of a bodily feature of an approximate head or face region of a viewer (e.g., the user) and selecting a region of interest for heart rate detection.

FIG. 5A illustrates an example 500 for detecting a representation of a bodily feature of an approximate head or face region 502 of a viewer (e.g., the user) and selecting a region of interest for heart rate detection. In this example, a detector 508 detects a representation of a right eye in image data captured by a camera of a computing device. A region of interest 504 corresponding to a portion of a forehead may then be selected for analysis (e.g., image data measurements of color, intensity, etc.) for heart rate detection.

Figure 5B:
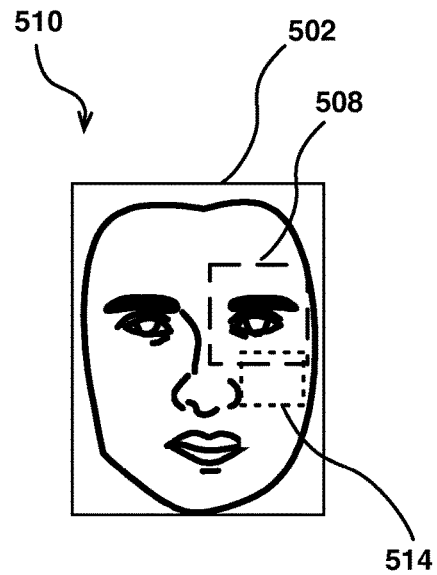
FIG. 5B illustrates an example for detecting a representation of a bodily feature of an approximate head or face region of the viewer and selecting a region of interest for heart rate detection.

FIG. 5B illustrates an example 510 for detecting a representation of a bodily feature of an approximate head or face region 502 of the viewer and selecting a region of interest for heart rate detection. Similar to the example 500 in FIG. 5A, the detector 508 detects a representation of a right eye in image data captured by a camera of a computing device. A region of interest 514 corresponding to a portion of a right cheek may then be selected for analysis for heart rate detection. In some embodiments, the examples 500 and 510 may be performed by a single camera, or, alternatively, with multiple cameras (e.g., a pair of stereoscopic cameras).

Figure 5C:
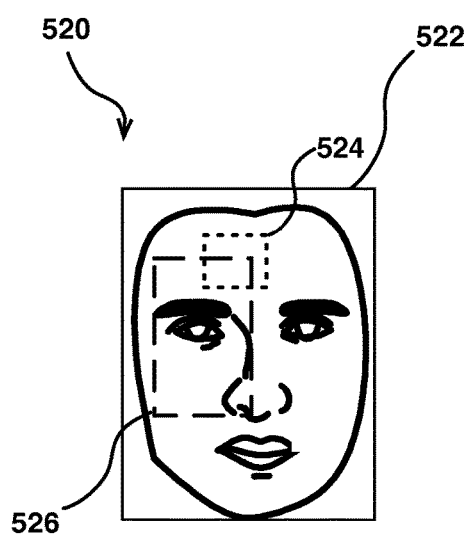
FIG. 5C illustrates an example for detecting a representation of a bodily feature of an approximate head or face region of a viewer (e.g., user) and selecting a region of interest for heart rate detection.

FIG. 5C illustrates an example 520 for detecting a representation of a bodily feature of an approximate head or face region 522 of a viewer (e.g., user) and selecting a region of interest for heart rate detection. In this example, a detector 526 detects a representation of a left eye in image data captured by a camera of a computing device. A region of interest 526 corresponding to a portion of a forehead may then be selected for analysis for heart rate detection.

Figure 5D:
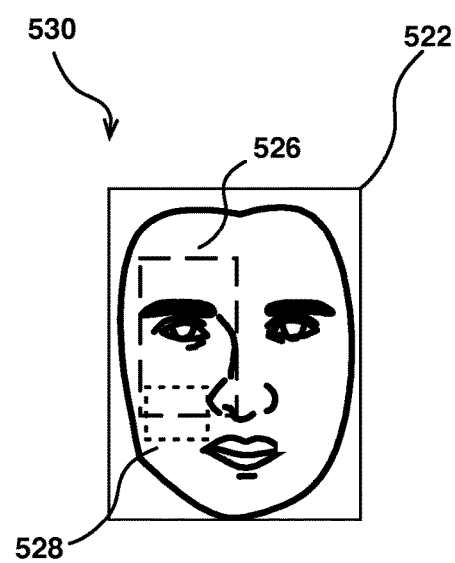
FIG. 5D illustrates an example for detecting a representation of a bodily feature of an approximate head or face region of the viewer and selecting a region of interest for heart rate detection.

FIG. 5D illustrates an example 530 for detecting a representation of a bodily feature of an approximate head or face region 522 of the viewer and selecting a region of interest for heart rate detection. In this example, a detector 526 detects a representation of the left eye in image data captured by a camera of a computing device. A region of interest 528 corresponding to a portion of a left cheek may then be selected for analysis for heart rate detection. In some embodiments, the examples 520 and 530 may be performed by a single camera, or, alternatively, with multiple cameras (e.g., a pair of stereoscopic cameras) similar to the examples 500 and 510 in FIGS. 5A and 5B.

As mentioned above, detection of the heart rate of the viewer may be performed by analyzing a selected region of interest of the representation of the face region of the viewer. This analysis includes determining image data measurements corresponding to color or intensity measurements that occur over time. More than one region of interest may be analyzed at the same time. For instance, the region of interest 504 or 524 corresponding to the forehead and the region of interest 514 or 528 corresponding to the right or left cheek may be analyzed at the same time. Due to motion of the viewer and/or other environment factors, the concurrent analysis of more than one region of interest may improve the detection of the heart rate when changes occur to the image data that is captured by the camera(s).

Figure 5E:
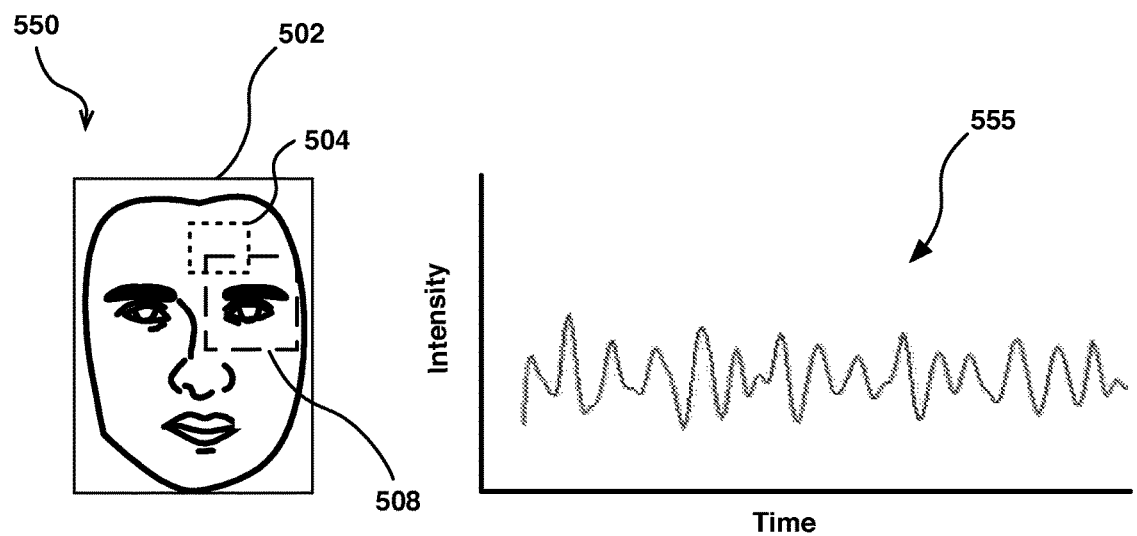
FIG. 5E illustrates an example for tracking image data measurements of the region of interest corresponding to a portion of the forehead that was selected as described in FIG. 5A.

FIG. 5E illustrates an example 550 for tracking image data measurements of the region of interest 504 corresponding to a portion of the forehead that was selected as described in FIG. 5A. An example graph 555 tracks image data measurements of the region of interest 504, such as intensity or brightness, over a period of time. A measure of intensity can correspond to one or more of the color channels (e.g., for an RGB image), or another brightness (e.g., in a case of a black/white or gray scale image), combination thereof, etc. In an example implementation of a heart rate detection algorithm, image data measurements of an average intensity of pixels in the region of interest 504 for a particular color channel(s), such as a green color channel, are determined. In an example, the green color channel may include the least amount of noise in a given image (e.g., when a RGB color camera includes a greater amount of pixels for green than red and/or blue). This example may assume that the image data is a 24-bit RGB image in which three color channels of red, green, and blue color are included, and that each color channel has 8 bits of information for red, green, and blue color channels. The average intensity for the color channel may be determined by taking a mean of values of intensities of the pixels in the region of interest (e.g., an intensity value of a patch including all pixels from the region of interest) to map color variations (e.g., intensity variations) over a period of time that correspond to a time-based pattern. In an embodiment, values corresponding to the color variations over time may also be amplified. A Fourier transform may then be performed on the information in the graph 555 to determine a heart rate of the viewer. In this example, the Fourier transform takes the time-based pattern or time domain signal (e.g., the graph 555) that could be expressed as a function f(t), and returns the overall frequency graph. The Fourier transform therefore may be understood as a mathematical transform that converts a mathematical function of time (e.g., the graph 555) into a function of frequency. When provided the overall frequency graph, a frequency value in the frequency domain with a highest amplitude value may be determined as the heart rate of the viewer (e.g., by filtering the frequency graph to select the frequency with the highest amplitude).

In another example heart rate detection algorithm, a heart rate may be detected using an Eulerian video magnification framework as proposed in 2012 by Hao-Yu Wu et al. In the Eulerian video magnification framework, a time series of color values at any spatial location (e.g., pixels from the region of interest 504) may be determined and these color values are then amplified in a given temporal frequency band of interest. For example, a band of temporal frequencies are amplified that includes possible human heart rates. The amplification may reveal the variation of redness as blood flows through the portion of the viewer's face corresponding to the region of interest 504. More specifically, pixels from the region of interest 504 may be separated into different spatial frequency bands. Temporal processing on each spatial band is then performed to determine a time series corresponding to the value of a pixel in a frequency band. A bandpass filter is applied on the time series to extract the frequency bands of interest. For example, frequencies within 0.4-4 Hz, corresponding to 24-240 beats per minute, may be selected to magnify a pulse. The temporal processing is uniform for all spatial levels, and for all pixels within each level. The extracted bandpassed signal is then multiplied by a given magnification factor. The magnified signal is then added to the original and a spatial pyramid is collapsed to obtain an output that indicates the heart rate of the viewer.

It is contemplated that other algorithms including different techniques may be utilized to detect a heart rate of a viewer and still be within the scope of the subject technology.

Figure 5F:
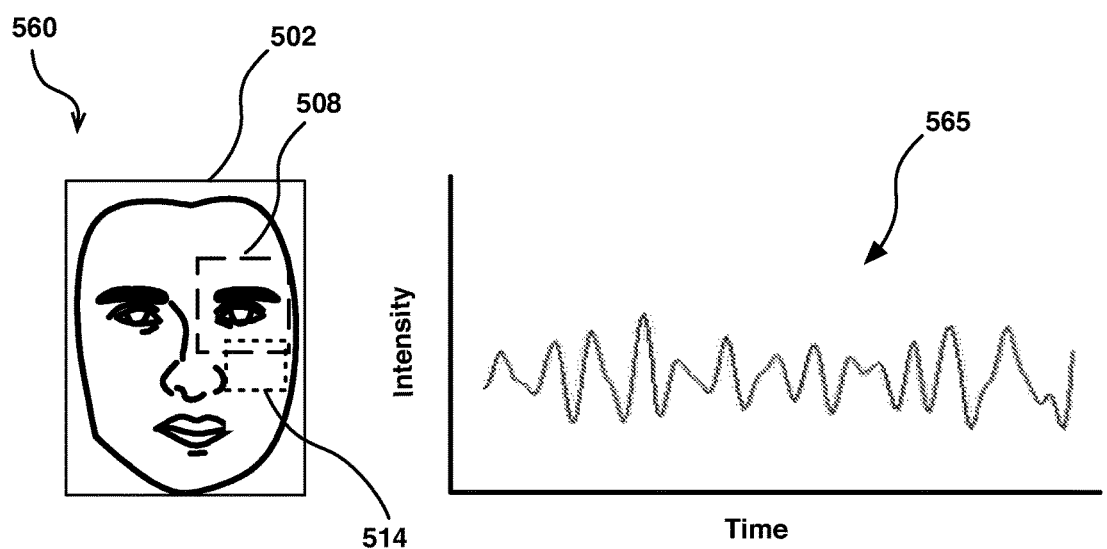
FIG. 5F illustrates an example for tracking image data measurements of the region of interest corresponding to a portion of the right cheek that was selected as described in FIG. 5B.

FIG. 5F illustrates an example 560 for tracking image data measurements of the region of interest 514 corresponding to a portion of the right cheek that was selected as described in FIG. 5B. Similarly, an example graph 555 over time tracks image data measurements of color over a period of time. As described above, the heart rate of the viewer may be determined using one or more of the aforementioned heart rate detection algorithms based on the image data measurements in the graph 555. Additionally, the image data measurements of different regions of interests may be combined or averaged to potentially improve heart rate detection. For example, values from the graphs 555 and 565 could be combined into a single graph that represents the mean values from both graphs. Thus, it is appreciated that image measurement values at respective region of interests may be combined from multiple cameras provided by a computing device. In another example, multiple sets of image data measurements from the same region of interest (e.g., only from the region of interest 504) may be combined or averaged. This may occur if image capture is interrupted or paused due to motion of the viewer, an occlusion blocking a field of view of a camera, or some other event or failure. Such combined image data measurement may then be fed into one or more heart rate detection algorithms for processing as described before.

Figure 6A:
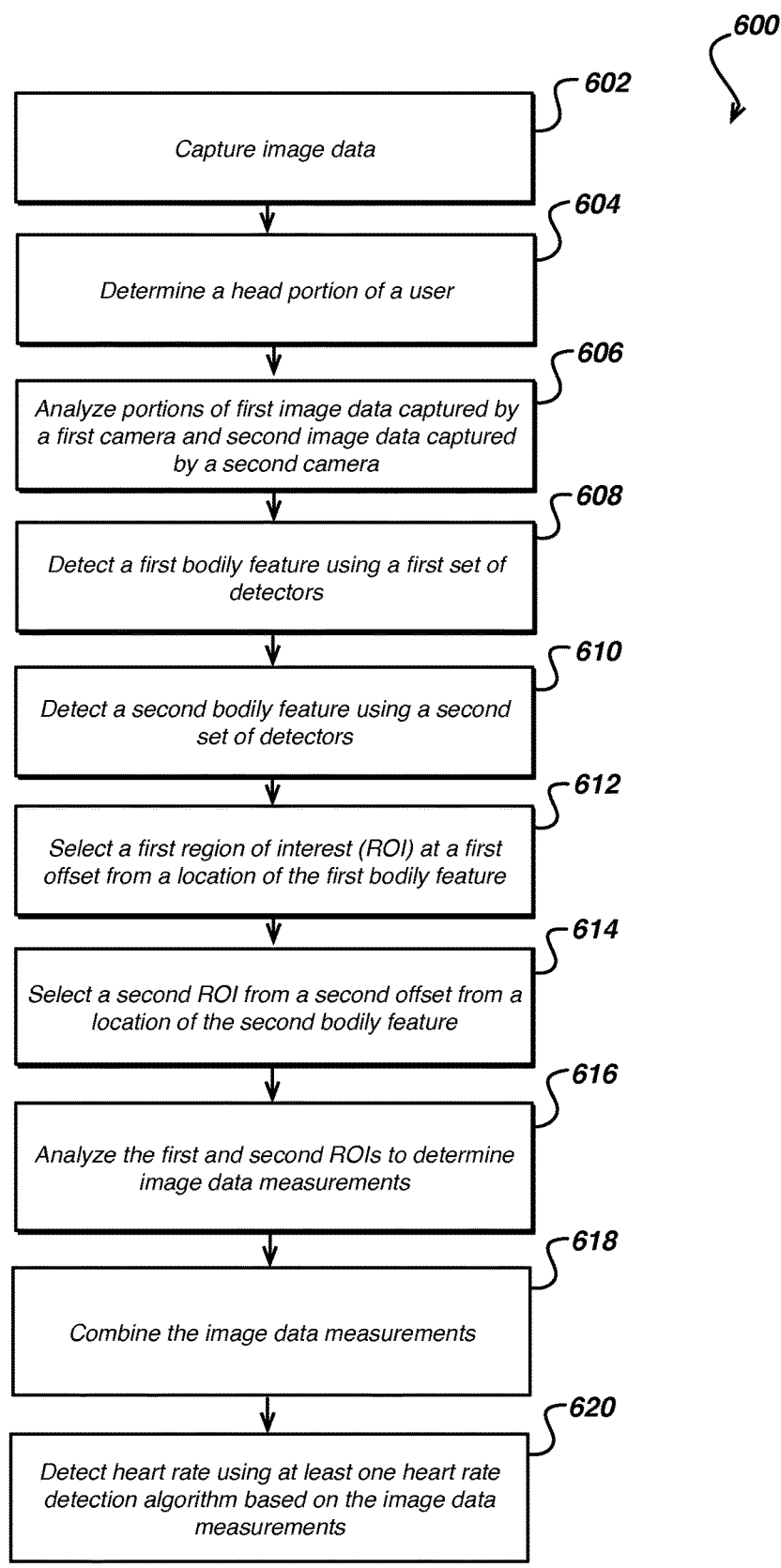
FIG. 6A illustrates an example process for detecting a heart rate of a viewer (e.g., user) of a computing device that can be utilized in accordance with various embodiments.

FIG. 6A illustrates an example process 600 for detecting a heart rate of a viewer (e.g., user) of a computing device that can be utilized in accordance with various embodiments. It should be understood that, for various processes discussed herein, there can be additional, fewer, or alternative steps performed in similar or alternative orders, or at least partially in parallel, in accordance with the various embodiments unless otherwise stated. In this example, head detection and/or tracking is activated on a computing device. The tracking can be activated at startup, upon opening an application, in response to a user action, or at any other appropriate time. Approaches for locating and tracking other objects can be used as well as discussed elsewhere herein. In this example, image data is captured 602. As discussed, this can include capturing three-dimensional image data including disparity information, or using a proximity sensor, structured light component, or other such component to capture distance information along with two-dimensional image data. Various other approaches can be used as well. In some embodiments, the image(s) can be acquired using one or more conventional cameras on a computing device, while in some embodiments the image(s) can be acquired using one or more relatively low power cameras, as may capture IR light at a relatively low resolution (e.g., 2MP or less) and color depth (e.g., monochrome) in at least some embodiments.

The image data can be analyzed to attempt to determine 604 a representation of a head portion of the user in the image data. Although the following example relates to the user of the device, it is appreciated that, instead of the user, a representation of a head portion of another person (e.g., a third person that may be the subject of the image captured from the camera) may be analyzed and still be within the scope of the subject technology. In an example, the representation of the head portion can correspond to a representation of the user's face. This analysis of the image data can include, for example, utilizing a face or head detection algorithm as discussed above to attempt to locate an approximate head or face position in a captured image or video frame. Once the head portion of the user is determined, portions of first image data captured by a first camera of the stereo camera pair and a second image captured by a second camera of the stereo camera pair can be analyzed 606 using a detector, template, or other classifier to attempt to identity feature points corresponding to facial features included in the representation of the user's face or other objects represented in the images. For example, the image data captured by a first camera of the pair of cameras can be analyzed by a first set of detectors to detect 608 a first bodily feature (e.g., a facial feature such as a right eye) in the head potion of a user of the computing device, where each detector of the first set of detectors can detect the first bodily feature using a different approach.

The image data captured by a second camera of the pair of cameras can be analyzed by a second set of detectors to detect 610 a second bodily feature (e.g., a facial feature such as a left eye) of the user, where like the first set of detectors, each detector of the second set of detectors can detect the second bodily feature using a different approach. As discussed before, in an embodiment, the respective image data captured by the first and second cameras may occur concurrently. The different approaches can include using different sized windows to detect facial features, different starting positions of the windows, etc. Other approaches can be used as well, such as to use shape, template, or object recognition processes such as a facial feature recognition process. In some embodiments, an object location algorithm might look for objects in the image data that meet a certain object detection criterion, such as objects (e.g., areas of a relatively common intensity in an image) of a certain size, shape, and/or location. In some embodiments, the image data represents infrared (IR) light emitted by the device, reflected by the object, and detected by the device.

A first region of interest (ROI) may be selected 612 using a first offset from the location of the first bodily feature (e.g., a facial feature corresponding to an eye, nose, cheek, etc., as discussed before). Similarly, a second ROI can be selected 614 using a second offset from the location of the second bodily feature. Image data information for pixels from the first and second ROIs may be analyzed 616 to determine respective sets of image data measurements. As discussed before, such image data measurements may include intensity measurements for pixels associated with the first and second ROIs that are at respective offsets from the first or second bodily features. The respective sets of image data measurements may be combined 618 (e.g., averaged, etc.). A heart rate may be detected 620 using at least one heart rate detection algorithm based at least in part on the combined image data measurements (as further described elsewhere herein).

Although the above example process 600 describes an approach for analyzing image data using two cameras, in another embodiment, the process 600 may use a single camera to determine both intensity change of pixel values within a region of interest and an offset from a bodily feature in a similar manner discussed above.

For tracking changes in head movement(s) of the user relative to the device, the subject technology may perform these additional operations to perform image data measurements based on such changes to detect the user's heart rate. In such embodiments, the head tracking may be used to adjust an offset for a region of interest pixels relative to a facial feature and, and once that region of interest is identified, the user's heart rate may be determined separately by analyzing pixel values associated to the region of interest. In accordance with at least an embodiment, a change in a relative location between a face of the user to the device may be determined. Using the first camera, a distance that the face of the user has moved based on the change in the relative location is determined. Based at least in part on the distance that the face of the user has moved, a first new offset from the location of the facial feature for analyzing a first new set of image data measurements is determined. Pixels in a region of interest that has been selected based at least on the first new offset may analyzed in accordance with the embodiments described herein to determine the user's heart rate. Additionally, in at least another embodiment, a second change in a second relative location between the face of the user to the device may be determined. Using the second camera, a second distance that the face of the user has moved based on the second change in the second relative location is determined. Based at least in part on the second distance that the face of the user has moved, a second new offset from the location of the facial feature for analyzing a second new set of image data measurements is determined. Further, pixels in a region of interest that has been selected based at least on the second new offset may analyzed in accordance with the embodiments described herein to determine the user's heart rate. Additionally, in an embodiment, the image data measurements from the regions of interests selected based at least on the first and second new offsets may be combined (e.g., averaged) to determine the user's heart rate as described before.

Figure 6B:
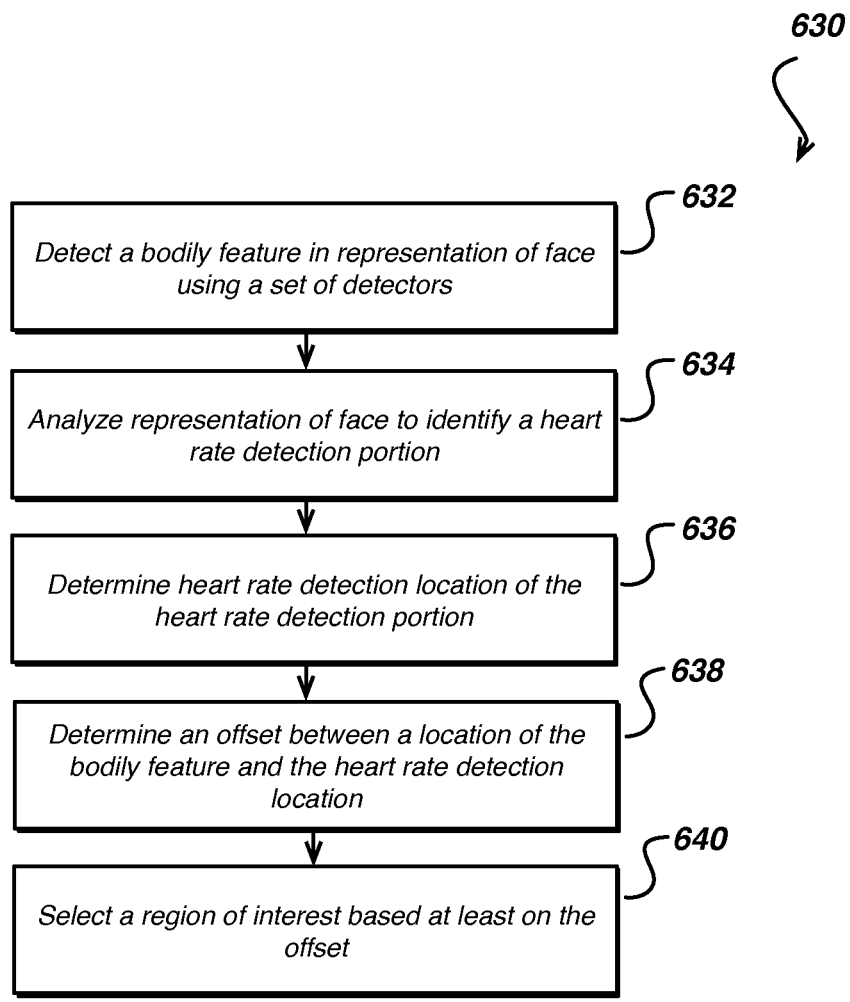
FIG. 6B illustrates an example process for selecting a region of interest in image data in accordance with various embodiments.

FIG. 6B illustrates an example process 630 for selecting a region of interest in image data in accordance with various embodiments. As discussed before, the image data may include a representation of the user's face in an embodiment. Further, the process 630 may be performed conjunctively with the process 600 in at least one embodiment. A bodily feature (e.g., a facial feature corresponding to one of a right or left eye, nose, chin, cheek, etc.) may be detected 632 in the representation of the user's face using at least one detector from a set of detectors in an embodiment. In one example, an eye location in the representation of the user's face is determined in which the eye location may be associated with a set of pixel values included in the representation of the face. As used herein, the eye location can correspond to a region of pixel values in the image data associated with pixel addresses representing the eye.

The representation of the face is analyzed 634 to identify a heart rate detection portion of the representation of the face. As used herein, a heart rate detection portion (e.g., a spot of skin located in the forehead, cheek, etc.) corresponds to a portion of the representation of the face where a best heart rate signal can be detected based on a given set of factors including current lighting, glare, facial hair, hats, obstructions, head hair, etc. This analysis step, in an embodiment, would occur over a period of time in which multiple images and/or face representations are analyzed. For example, a first image could be analyzed to determine a first heart rate detection portion at a first time, a second image could be analyzed to determine a second heart rate detection portion at a second subsequent time, and a third image could be analyzed to determine a third heart rate detection portion at a third subsequent time from the second subsequent time. It is appreciated that the aforementioned heart rate detection portions at different times may correspond to substantially the same location within the representation of the user's face in an embodiment.

A heart rate detection location of the heart rate detection portion is determined 636, where the heart rate detection location may be associated with a set of pixel values included in the representation of the face. As used herein, a heart rate detection location refers to a region of pixel values in image data associated with pixel addresses representing the spot of skin where heart rate monitoring is focused.

An offset may be determined 638 from a location of the detected bodily feature (e.g., the aforementioned eye location). In an embodiment, the offset may include a number of pixels between the eye location (e.g., the location of the detected bodily feature) and the heart rate detection location in the representation of the face. A region of interest is selected 636 based at least on the offset. In an example, the selected region of interest may substantially include the region of pixel values in the image data associated with pixel addresses representing the spot of skin where heart rate monitoring is focused. In another example, the selected region of interest may be a subset of aforementioned region of pixel values in the image data.

In at least another embodiment, for tracking a facial feature(s) when the perspective of the user's face may change depending on the user's movement(s) and/or device movement(s), the subject technology may provide the following implementation. After the user's face is located as described in accordance with embodiments herein, a facial feature is detected (e.g., an eye). An anchor point for the detected facial feature may be determined. The anchor point may be a pixel included in a set of pixels associated with the detected facial feature. In an embodiment, the anchor point may be arbitrarily selected as some point or pixel among a set of pixels corresponding to the facial feature, or some other position such as a center point among the set of pixels. A location (e.g., forehead) that is likely to be feasible for monitoring a heart rate is determined (e.g., a heart rate detection location). A first offset between pixels associated with the detected feature (e.g., the eye) and pixels associated with the heart rate detection location is then determined. In an embodiment, the first offset is determined based on a center point of the heart rate detection portion and then used in conjunction with movement to track the heart rate detection location as the device moves relative to the face. Next, it is determined that the computing device is moving relative to the face. A second offset is determined based at least in part on device movement and the first offset. A new set of pixels associated with a new location (e.g., cheek) is determined based on the second offset and pixels associated with a facial feature at the new location.

Figure 7:
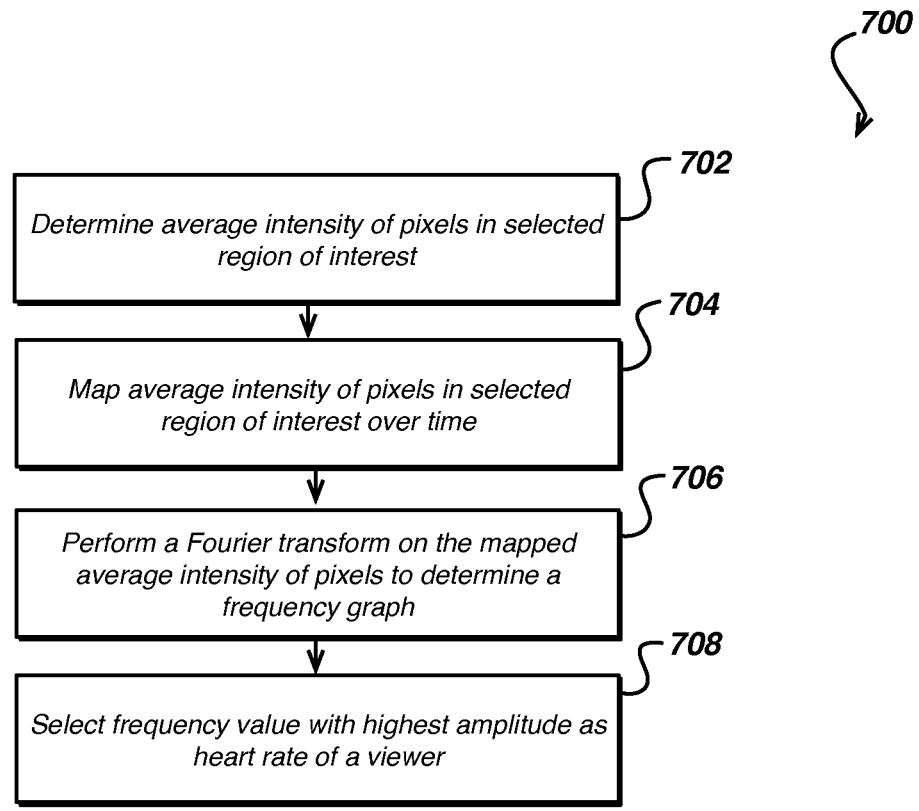
FIG. 7 illustrates an example process for detecting a user's heart rate using a set of operations on pixels included in a given region of interest in accordance with various embodiments.

FIG. 7 illustrates an example process 700 for detecting a user's heart rate using a set of operations on pixels included in a given region of interest in accordance with various embodiments. The process 700 may be performed conjunctively with the processes 600 and/or 630 in at least one embodiment. An average intensity of pixels in a selected region of interest may be determined 702. The average intensity of pixels may be mapped 704 over a period of time. A Fourier transform operation may be performed 706 on the mapped average intensity of pixels to determine a frequency graph. A frequency value with a highest amplitude may be selected 708 as a heart rate of the viewer (e.g., user).

Figure 8:
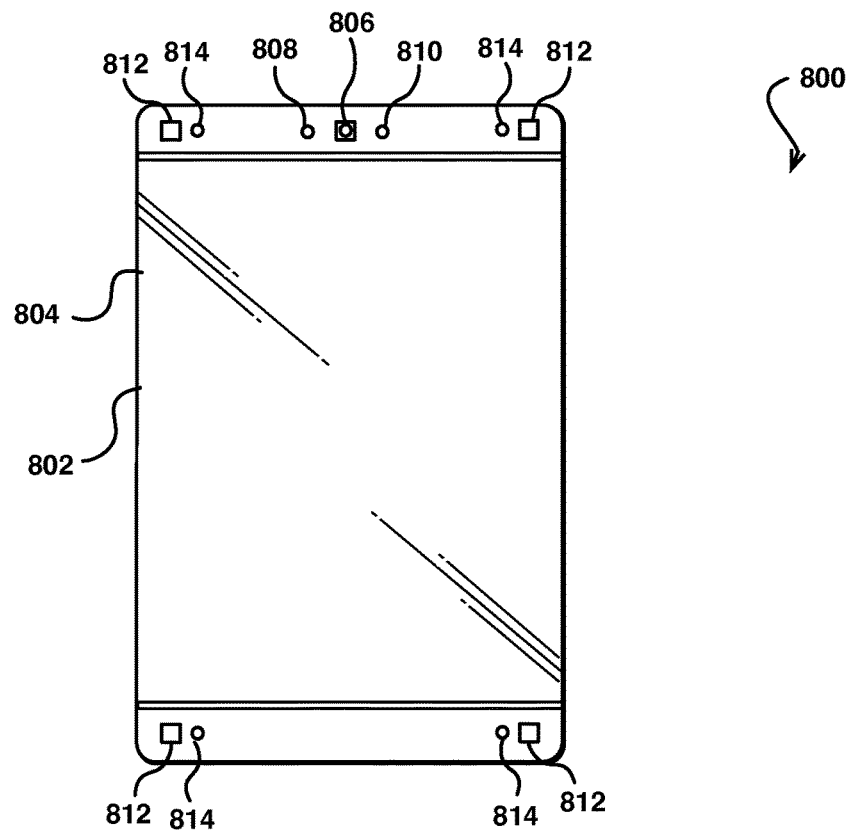
FIG. 8 illustrates an example computing device that can be utilized in accordance with various embodiments.

FIG. 8 illustrates a front view 800 of an example computing device 802 that can be used to perform methods in accordance with various embodiments discussed and suggested herein. In this example, the device has a front-facing camera 806 (i.e., a camera on the same side of the device as a display screen 804) that can be used for purposes such as video conferencing. Along with the camera, the device can also have elements such as a light sensor 808 for determining an amount of ambient light around the device, and a white light LED 810 or other such light source capable of operating as a flash, or otherwise providing light for the front-facing camera 806. The computing device also includes four cameras 812, which in this example can have a lower resolution, power requirement, and/or color depth than the front-facing camera 806. Such sensors can be used for purposes such as head tracking and gesture input, for example, which can require image data to be captured over a period of time but do not require full or higher resolution images. Along with each (or at least some) of these cameras 812 can also be a light source, such as an IR LED 814, that can emit IR that, when reflected, can be directed back toward at least the associated camera 812. Placing the LEDs near the sensors can have the advantage that objects, such as human eyes, that function as retro-reflectors can enable those objects to be detected by the adjacent sensors in the captured image data. In at least some embodiments, the distance between a camera and an LED can be at least 1-2 mm. It should be understood that reference numbers for similar elements can be used within a figure, or carried over between figures, for purposes of explanation and ease of understanding, but that such use should not be read as a limitation on the scope of the various embodiments unless otherwise stated.

Figure 9:
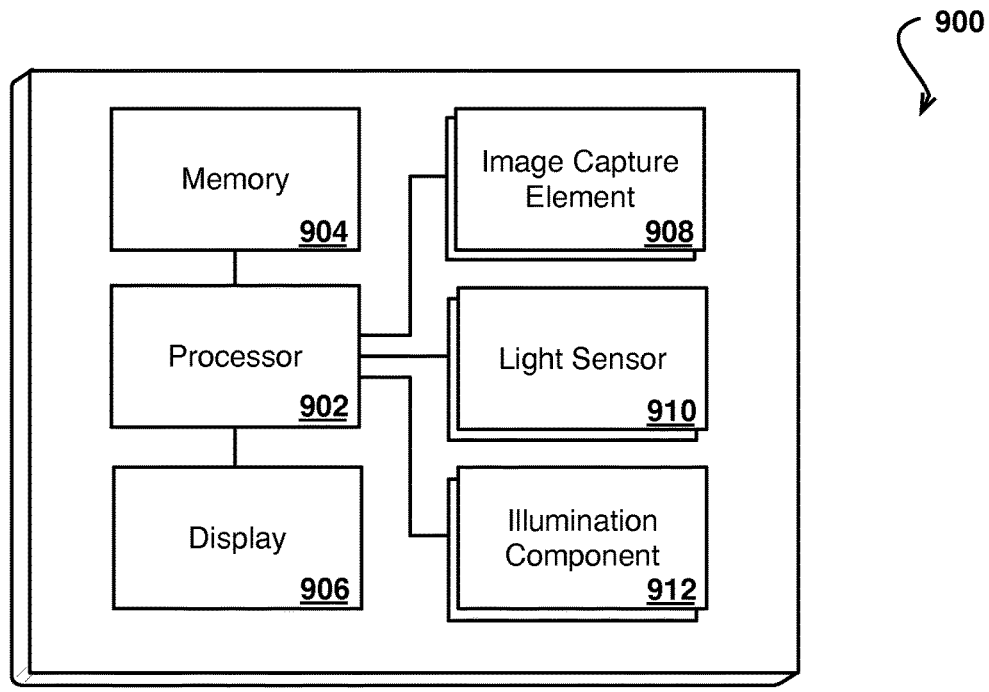
FIG. 9 illustrates an example set of basic components of a portable computing device, such as the device described with respect to FIG. 8.

In order to provide various functionality described herein, FIG. 9 illustrates an example set of basic components of a computing device 900, such as the device 802 described with respect to FIG. 8. In this example, the device includes at least one central processor 902 for executing instructions that can be stored in at least one memory device or element 904. As would be apparent to one of ordinary skill in the art, the device can include many types of memory, data storage or non-transitory computer-readable storage media, such as a first data storage for program instructions for execution by the processor 902, the same or separate storage can be used for images or data, a removable storage memory can be available for sharing information with other devices, etc. The device typically will include some type of display element 906, such as a touch screen, electronic ink (e-ink), organic light emitting diode (OLED) or liquid crystal display (LCD), although devices such as portable media players might convey information via other means, such as through audio speakers. In at least some embodiments, the display screen provides for touch or swipe-based input using, for example, capacitive or resistive touch technology.

As discussed, the device in many embodiments will include at least two image capture elements 908, such as two or more cameras (or at least one stereoscopic camera) that are able to image a user, people, or objects in the vicinity of the device. An image capture element can include, or be based at least in part upon any appropriate technology, such as a CCD or CMOS image capture element having a determined resolution, focal range, viewable area, and capture rate. The image capture elements can also include at least one IR sensor or detector operable to capture image information for use in determining gestures or motions of the user. The example computing device includes at least one light sensor 910 which determine the need for light when capturing an image, among other such functions. The example device 900 includes at least one illumination component 912, as may include one or more light sources (e.g., white light LEDs, IR emitters, or flash lamps) for providing illumination and/or one or more light sensors or detectors for detecting ambient light or intensity, etc.

The example device can include at least one additional input device able to receive conventional input from a user. This conventional input can include, for example, a push button, touch pad, touch screen, wheel, joystick, keyboard, mouse, trackball, keypad or any other such device or element whereby a user can input a command to the device. These I/O devices could even be connected by a wireless infrared or Bluetooth or other link as well in some embodiments. In some embodiments, however, such a device might not include any buttons at all and might be controlled only through a combination of visual (e.g., gesture) and audio (e.g., spoken) commands such that a user can control the device without having to be in contact with the device.

The device also can include at least one orientation or motion sensor. As discussed, such a sensor can include an accelerometer or gyroscope operable to detect an orientation and/or change in orientation, or an electronic or digital compass, which can indicate a direction in which the device is determined to be facing. The mechanism(s) also (or alternatively) can include or comprise a global positioning system (GPS) or similar positioning element operable to determine relative coordinates for a position of the computing device, as well as information about relatively large movements of the device. The device can include other elements as well, such as may enable location determinations through triangulation or another such approach. These mechanisms can communicate with the processor, whereby the device can perform any of a number of actions described or suggested herein.

Figure 10:
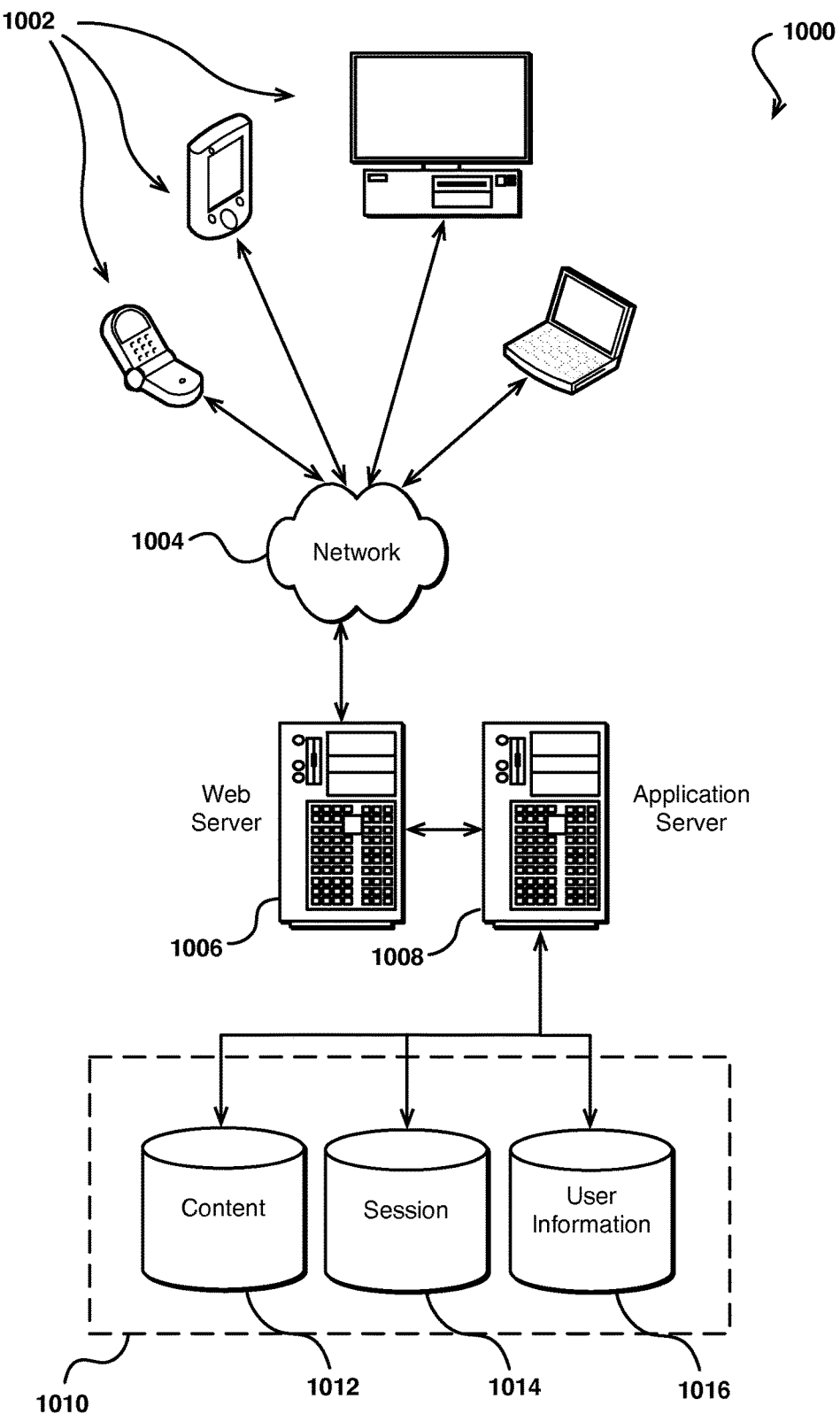
FIG. 10 illustrates an example environment in which aspects of the various embodiments can be implemented.

As discussed, different approaches can be implemented in various environments in accordance with the described embodiments. For example, FIG. 10 illustrates an example of an environment 1000 for implementing aspects in accordance with various embodiments. As will be appreciated, although a Web-based environment is used for purposes of explanation, different environments may be used, as appropriate, to implement various embodiments. The system includes an electronic client device 1002, which can include any appropriate device operable to send and receive requests, messages or information over an appropriate network 1004 and convey information back to a user of the device. Examples of such client devices include personal computers, cell phones, handheld messaging devices, laptop computers, set-top boxes, personal data assistants, electronic book readers and the like. The network can include any appropriate network, including an intranet, the Internet, a cellular network, a local area network or any other such network or combination thereof. Components used for such a system can depend at least in part upon the type of network and/or environment selected. Protocols and components for communicating via such a network are well known and will not be discussed herein in detail. Communication over the network can be enabled via wired or wireless connections and combinations thereof. In this example, the network includes the Internet, as the environment includes a Web server 1006 for receiving requests and serving content in response thereto, although for other networks an alternative device serving a similar purpose could be used, as would be apparent to one of ordinary skill in the art.

The illustrative environment includes at least one application server 1008 and a data store 1010. It should be understood that there can be several application servers, layers or other elements, processes or components, which may be chained or otherwise configured, which can interact to perform tasks such as obtaining data from an appropriate data store. As used herein the term "data store" refers to any device or combination of devices capable of storing, accessing and retrieving data, which may include any combination and number of data servers, databases, data storage devices and data storage media, in any standard, distributed or clustered environment. The application server can include any appropriate hardware and software for integrating with the data store as needed to execute aspects of one or more applications for the client device and handling a majority of the data access and business logic for an application. The application server provides access control services in cooperation with the data store and is able to generate content such as text, graphics, audio and/or video to be transferred to the user, which may be served to the user by the Web server in the form of HTML, XML or another appropriate structured language in this example. The handling of all requests and responses, as well as the delivery of content between the client device 1002 and the application server 1008, can be handled by the Web server 1006. It should be understood that the Web and application servers are not required and are merely example components, as structured code discussed herein can be executed on any appropriate device or host machine as discussed elsewhere herein.

The data store 1010 can include several separate data tables, databases or other data storage mechanisms and media for storing data relating to a particular aspect. For example, the data store illustrated includes mechanisms for storing production data 1012 and user information 1016, which can be used to serve content for the production side. The data store also is shown to include a mechanism for storing log or session data 1014. It should be understood that there can be many other aspects that may need to be stored in the data store, such as page image information and access rights information, which can be stored in any of the above listed mechanisms as appropriate or in additional mechanisms in the data store 1010. The data store 1010 is operable, through logic associated therewith, to receive instructions from the application server 1008 and obtain, update or otherwise process data in response thereto. In one example, a user might submit a search request for a certain type of element. In this case, the data store might access the user information to verify the identity of the user and can access the catalog detail information to obtain information about elements of that type. The information can then be returned to the user, such as in a results listing on a Web page that the user is able to view via a browser on the user device 1002. Information for a particular element of interest can be viewed in a dedicated page or window of the browser.

Each server typically will include an operating system that provides executable program instructions for the general administration and operation of that server and typically will include computer-readable medium storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 10. Thus, the depiction of the system 1000 in FIG. 10 should be taken as being illustrative in nature and not limiting to the scope of the disclosure.

As discussed above, the various embodiments can be implemented in a wide variety of operating environments, which in some cases can include one or more user computers, computing devices, or processing devices which can be used to operate any of a number of applications. User or client devices can include any of a number of general purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Various aspects also can be implemented as part of at least one service or Web service, such as may be part of a service-oriented architecture. Services such as Web services can communicate using any appropriate type of messaging, such as by using messages in extensible markup language (XML) format and exchanged using an appropriate protocol such as SOAP (derived from the "Simple Object Access Protocol"). Processes provided or executed by such services can be written in any appropriate language, such as the Web Services Description Language (WSDL). Using a language such as WSDL allows for functionality such as the automated generation of client-side code in various SOAP frameworks.

Most embodiments utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In embodiments utilizing a Web server, the Web server can run any of a variety of server or mid-tier applications, including HTTP servers, FTP servers, CGI servers, data servers, Java servers, and business application servers. The server(s) also may be capable of executing programs or scripts in response requests from user devices, such as by executing one or more Web applications that may be implemented as one or more scripts or programs written in any programming language, such as Java®, C, C# or C++, or any scripting language, such as Perl, Python, or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:

1. A computing device, comprising:
    a processor;
    a first camera having a first field of view;
    a second camera separated by a distance from the first camera, the second camera having a second field of view that at least partially overlaps the first field of view; and
    memory device including instructions that, when executed by the processor, cause the computing device to:
        capture first image data using the first camera and second image data using the second camera, the first image data and the second image data being captured concurrently;
        analyze the first image data to determine a first representation of a face corresponding to a user of the computing device;
        analyze the second image data to determine a second representation of the face;
        analyze the first representation of the face using a first facial feature recognition algorithm;
        determine an eye location in the first representation of the face, the eye location associated with a first set of pixel values included in the first representation of the face;
        analyze the first representation of the face to identify a heart rate detection portion of the first representation of the face;
        determine a heart rate detection location of the heart rate detection portion, the heart rate detection location associated with a second set of pixel values included in the first representation of the face; and
        determine a first offset between the eye location and the heart rate detection location, the first offset comprising a number of pixels between the eye location and the heart rate detection location in the first representation of the face.

2. The computing device of claim 1, wherein the instructions further cause the processor to:
    determine a first change in a first relative location between the first representation of the face of the user to the computing device;
    determine, using the first camera, a first distance that the first representation of the face of the user has moved based on the first change in the first relative location; and
    determine, based at least in part on the first distance that the first representation of the face of the user has moved, a first new offset from the location of the first representation of the first facial feature for analyzing a first set of image data measurements, the first set of image data measurements being used to determine a heart rate of the user.

3. The computing device of claim 1, wherein the instructions further cause the processor to:
    determine a first set of image data measurements of the heart rate detection location, wherein the first set of image data measurements comprise pixel values of a set of pixels within the heart rate detection location, the heart rate detection location having a center point that is determined based on the first offset from the eye location;
    determine, using the first camera, a first distance that the first representation of the face of the user has moved based on the first change in a first relative location between the first representation of the face of the user to the computing device;
    determine a second offset based on the first distance and the first offset;

determine a new set of pixels associated with a new location in the first representation of the face of the user based at least in part on the second offset and pixels associated with a new facial feature at the new location; and determine a second set of image data measurements of the new set of pixels, wherein the second set of image data measurements comprise pixel values of the new set of pixels.

4. The computing device of claim 3, wherein to determine the first set of image data measurements further causes the computing device to:

analyze the pixels values associated with the set of pixels of the heart rate detection location to determine color variations at a range of frequencies over a period of time;

amplify the color variations at the range of frequencies; and filter the amplified color variations to determine a heart rate of the user.

5. A computing device, comprising:

a processor;

a camera configured to capture image data; and memory device including instructions that, when executed by the processor, cause the computing device to:

capture the image data using the camera, the image data including a head representation of a head portion of a person;

determine a feature representation of a first bodily feature of the head portion;

determine a region of interest in the head representation based on an offset from the feature representation;

analyze pixel values associated with the region of interest to determine first image data measurements over time; and determine a heart rate of the person based at least in part on the first image data measurements.

6. The computing device of claim 5, further comprising:

a second camera, the second camera having a field of view that at least partially overlaps a first field of view of the camera, wherein the instructions, when executed further enable the computing device to:

capture second image data using the second camera, the second image data including a second head representation of the head portion of the person;

determine a second feature representation of a second bodily feature of the head portion in the second image data;

determine a second region of interest in the second head representation based on a second offset from the second feature representation; and analyze second pixel values associated with the second region of interest to determine second image data measurements over time.

7. The computing device of claim 6, wherein to detect the heart rate of the person further causes the computing device to:

determine average image data measurements based at least in part on the first image data measurements and the second image data measurements; and detect the heart rate of the person using at least the average image data measurements.

8. The computing device of claim 5, wherein the offset from the feature representation is based at least on one of a location of facial foramen or a location of an artery or vein in the head representation.

9. The computing device of claim 5, wherein to analyze pixel values associated with the region of interest to determine first image data measurements over time, further causes the computing device to:

determine an average intensity of the pixel values in the region of interest; and associate the average intensity of the pixel values in the region of interest over time to determine to a time-based graph of the average intensity of the pixel values.

10. The computing device of claim 9, wherein to detect the heart rate of the person using at least the average image data measurements, further causes the computing device to:

perform a transform operation on the time-based graph to determine a frequency graph; and select a frequency value with a highest amplitude from the frequency graph as the heart rate of the person.

11. The computing device of claim 5, wherein the instructions, when executed further enable the computing device to:

determining movement of the computing device relative to the head representation; and determining a second offset associated with the movement.

12. The computing device of claim 5, wherein the bodily feature includes at least one of the person's eye, nose, mouth, or other features associated with the person.

13. The computing device of claim 6, further comprising:

determine a first change in a first relative location between the head representation to the computing device;

determine, using the camera, a first distance that the feature representation has moved based on the first change in the first relative location; and determine, based at least in part on the first distance that the feature representation has moved, a first new offset from the location of the feature representation for analyzing a first new set of image data measurements of new pixels values associated with the region of interest at the first new offset.

14. The computing device of claim 5, wherein at least one detector from a set of detectors is used to detect the feature representation, the at least one detector having a geometric shape in a size measured in pixels, the pixels being a portion of a total number of pixels of the image data.

15. A non-transitory computer-implemented method, comprising:

capturing image data using a camera, the image data including a head representation of a head portion of a user of a computing device;

determining a feature representation of a first bodily feature of the head portion;

determining a region of interest in the head representation based on an offset from the feature representation;

analyzing pixel values associated with the region of interest to determine first image data measurements over time; and determining a heart rate of the person based at least in part on the first image data measurements.

16. The non-transitory computer-implemented method of claim 15, further comprising:

capturing second image data using a second camera, the second image data including a second head representation of the head portion of the person;

detecting a second feature representation of a second bodily feature of the head portion in the second image data;

determining a second region of interest in the second head representation based on a second offset from the second feature representation; and analyzing second pixel values associated with the second region of interest to determine second image data measurements over time.

17. The non-transitory computer-implemented method of claim 16, wherein to detect the heart rate of the user further comprises:

determine average image data measurements over time based on the first image data measurements and the second image data measurements; and detecting the heart rate of the person using at least the average image data measurements.

18. The non-transitory computer-implemented method of claim 15, wherein the offset from the feature representation is based at least on one of a location of facial foramen or a location of an artery or vein in the head representation.

19. The non-transitory computer-implemented method of claim 15, wherein to analyze pixel values associated with the region of interest to determine first image data measurements over time, further comprises:

determining an average intensity of the pixel values in the region of interest; and associate the average intensity of the pixel values in the region of interest over time to determine to a time-based graph of the average intensity of the pixel values.

20. The non-transitory computer-implemented method of claim 19, wherein to detect the heart rate of the user using at least the average image data measurements, further comprises:

performing a transform operation on the time-based graph to determine a frequency graph; and selecting a frequency value with a highest amplitude from the frequency graph as the heart rate of the user.

* * * * *